(12) United States Patent
Ishii et al.

(10) Patent No.: US 7,745,654 B2
(45) Date of Patent: Jun. 29, 2010

(54) PROCESS FOR THE PREPARATION OF VINYL- OR ALLYL-CONTAINING COMPOUNDS

(75) Inventors: Yasutaka Ishii, Takatsuki (JP); Tatsuya Nakano, Himeji (JP); Takahiro Iwahama, Himeji (JP)

(73) Assignee: Daicel Chemical Industries, Ltd., Sakai-Shi (JP)

( * ) Notice: Subject to any disclaimer, the term of this patent is extended or adjusted under 35 U.S.C. 154(b) by 460 days.

(21) Appl. No.: 11/713,024

(22) Filed: Mar. 2, 2007

(65) Prior Publication Data
US 2007/0213549 A1 Sep. 13, 2007

(30) Foreign Application Priority Data
Mar. 10, 2006 (JP) .............................. 2006-066531

(51) Int. Cl.
C07F 7/04 (2006.01)
(52) U.S. Cl. .................................................. 556/465
(58) Field of Classification Search ................ None
See application file for complete search history.

(56) References Cited

U.S. PATENT DOCUMENTS 5,908,943 A 6/1999 Au et al.
6,780,952 B2 * 8/2004 Paul et al. .................... 526/320

OTHER PUBLICATIONS

Fleming et al., Stereocontrol in organic synthesis using silicon-containing compounds. A formal synthesis of prostaglandins controlling the stereochemistry at C-15 using a silyl-to-hydroxy conversion following a stereochemically convergent synthesis of an allylsilane, Journal of the Chemical Society, Perkin Transactions 1: Organic and Bio-Organic Chemistry (1998), (17), 2687-2700}.*
Takeuchi et al., Organic Letters, American Chemical Society,1999, vol. 1, No. 2, pp. 265-267. (XP002282722) ISSN: 1523-7060.
Kitagawa et al., Organic Letter, American Chemical Society,2004, vol. 6, No. 20, pp. 3605-3607. (XP002448323) ISSN:1523-7060.
Watson et al., Journal of the American Chemical Society,2004, vol. 126 No. 16, pp. 5086-5087, (XP002448324) ISSN:0002-7863.
Fihri et al., Advance Synthesis & Catalysis, 2005, vol. 347 No. 9, pp. 1198-1202, XP002448325 ISSN:1615-4150.
Watson et al., Journal of the American Chemical Society,2005, vol. 127 No. 49, pp. 17516-17529, (XP002448326) ISSN:0002-7863.
Takahashi et al., Bulletin of the Chemical Society of Japan, 1972, vol. 45 No. 1, pp. 230-236. (XP009031594) ISSN:0009-2673.
Murahashi et al., Tetrahedron Letters, 1988, vol. 29 No. 24 pp. 2973-2976. (XP002448327) ISSN:0040-4039.
Feuerstein et al., Chemical Communications, 2001, pp. 43-44, (XP002448328) ISSN:1359-7345.
Rosenberg et al. J. Org. Chem., vol. 22, Oct. 1957, pp. 1200-1202.
Schlosser et al. Tetrahedron, vol. 45, No. 9, pp. 2649-2664, 1989.
Vasilieva et al., Russian Chemical Bulletin vol. 49, No. 3, Mar. 2000, pp. 431-437.

* cited by examiner

*Primary Examiner*—Jafar Parsa
*Assistant Examiner*—Chukwuma O Nwaonicha
(74) *Attorney, Agent, or Firm*—Birch, Stewart, Kolasch & Birch, LLP

(57) ABSTRACT

A vinyl- or allyl-containing compound represented by following Formula (3):

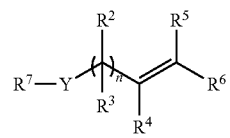

(3)

wherein $R^2$, $R^3$, $R^4$, $R^5$, and $R^6$ each represent hydrogen atom or a nonmetallic atom-containing group; $R^7$ represents a nonmetallic atom-containing group; Y represents a group selected from the group consisting of —Si($R^8$)($R^9$)—, —Si($R^{10}$)($R^{11}$)—O—, the left hand of which is combined with $R^7$, and —N$R^{12}$—, wherein $R^8$, $R^9$, $R^{10}$, $R^{11}$, and $R^{12}$ each represent hydrogen atom or a nonmetallic atom-containing group; and "n" represents 0 or 1, is prepared by reacting a vinyl or allyl ester compound represented by following Formula (1):

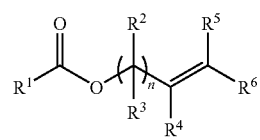

(1)

wherein $R^1$ represents hydrogen atom or a nonmetallic atom-containing group; $R^2$, $R^3$, $R^4$, $R^5$, $R^6$, and "n" are as defined above, with a compound represented by following Formula (2):

$$R^7\text{—Y—H} \qquad (2)$$

wherein $R^7$ and Y are as defined above, in the presence of a transition element compound.

1 Claim, No Drawings

PROCESS FOR THE PREPARATION OF VINYL- OR ALLYL-CONTAINING COMPOUNDS

BACKGROUND OF THE INVENTION

1. Field of the Invention

The present invention relates to a process for the preparation of vinyl- or allyl-containing compounds. Such vinyl- or allyl-containing compounds are useful typically as semiconductor materials, raw materials for functional polymers, intermediates for the synthetic preparation of fine chemicals such as pharmaceutical preparations and agricultural chemicals, and intermediate materials for organic chemicals.

2. Description of the Related Art

Certain processes have been known as processes for the preparation of vinyl- or allyl-containing silicon compounds or amine compounds such as vinylsilanes, allylsilanes, silyl vinyl ethers, silyl allyl ethers, and allylamines. Allylsilanes or vinylsilanes, for example, have been prepared by reacting chlorosilane with an allyl (or vinyl) magnesium Grignard reagent (J. Org. Chem., 1957, 22, 1200). Chlorosilane used in this process, however, is difficult to handle. In addition, such allyl (or vinyl) magnesium Grignard reagents (allylating or vinylating agents) are expensive. Silyl vinyl ethers or silyl allyl ethers have been prepared, for example, by using chlorosilane as a raw material (Tetrahedron, 1989, 45, 2649). This process also uses chlorosilane which is difficult to handle, as in the above-mentioned process. Diallylamine has been prepared, for example, by a process of reacting allyl chloride with a primary amine (Russ. Chem. Bl., 2000, 49, 431). This process, however, uses an equivalent amount of sodium hydroxide and thereby invites by-production of a large quantity of salts.

SUMMARY OF THE INVENTION

Under these circumstances, it is desirable to provide a process for easily and conveniently preparing vinyl- or allyl-containing silicon compounds or amine compounds in good yields under mild conditions. Such vinyl- or allyl-containing silicon compounds or amine compounds include vinylsilanes, allylsilanes, silyl vinyl ethers, silyl allyl ethers, and allylamines.

It is also desirable to provide a process for industrially efficiently preparing vinyl- or allyl-containing silicon compounds or amine compounds through a catalytic reaction using raw materials that are inexpensive and easy to handle.

After intensive investigations, the present inventors have found that a vinyl- or allyl-containing silicon compound or amine compound can be easily and conveniently prepared under mild conditions by reacting a corresponding vinyl or allyl ester compound typically with a silane compound, silanol compound, or a primary or secondary amine in the presence of a specific catalyst. The present invention has been made based on these findings.

According to an embodiment of the present invention, there is provided a process for the preparation of a vinyl- or allyl-containing compound represented by following Formula (3):

wherein $R^2$, $R^3$, $R^4$, $R^5$, and $R^6$ are the same as or different from one another and each represent hydrogen atom or a nonmetallic atom-containing group; $R^7$ represents a nonmetallic atom-containing group; Y represents a group selected from the group consisting of $-Si(R^8)(R^9)-$, $-Si(R^{10})(R^{11})-O-$, the left hand of which is combined with $R^7$, and $-NR^{12}-$, wherein $R^8$, $R^9$, $R^{10}$, $R^{11}$, and $R^{12}$ are the same as or different from one another and each represent hydrogen atom or a nonmetallic atom-containing group; and "n" represents 0 or 1. The process includes the step of carrying out a reaction between a vinyl or allyl ester compound represented by following Formula (1):

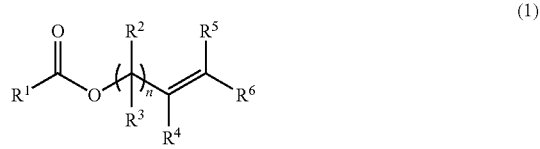

wherein $R^1$ represents hydrogen atom or a nonmetallic atom-containing group; $R^2$, $R^3$, $R^4$, $R^5$, $R^6$, and "n" are as defined above, and a compound represented by following Formula (2):

wherein $R^7$ and Y are as defined above, in the presence of at least one transition element compound.

The transition element compounds include, for example, compounds of Group VIII elements of the Periodic Table of Elements such as iridium compounds. Compounds represented by Formula (2) include silane compounds, silanol compounds, primary amines, and secondary amines.

The vinyl or allyl ester compounds and vinyl- or allyl-containing compounds as used herein also include corresponding compounds except with one or more substituents replacing hydrogen atoms of vinyl group ($-CH=CH_2$) or allyl group ($-CH_2-CH=CH_2$)

According to an embodiment of the present invention, vinyl- or allyl-containing silicon compounds or amine compounds can be easily and conveniently prepared in good yields under mild conditions, and the vinyl- or allyl-containing silicon compounds or amine compounds can be industrially efficiently prepared from inexpensive and easy-to-handle raw materials through a catalytic reaction. Such vinyl- or allyl-containing silicon compounds or amine compounds include vinylsilanes, allylsilanes, silyl vinyl ethers, silyl allyl ethers, and allylamines.

DESCRIPTION OF THE PREFERRED EMBODIMENTS

Transition Element Compounds

According to an embodiment of the present invention, one or more transition element compounds, including elementary substances of transition elements, are used as catalysts. Each of these transition element compounds can be used alone or in combination. Transition elements include Group IIIA elements such as lanthanum and cerium, of which lanthanoid elements are preferred; Group IVA elements such as titanium and zirconium; Group VA elements such as vanadium; Group VIA elements such as chromium, molybdenum, and tungsten; Group VIIA elements such as manganese; Group VIII elements such as iron, cobalt, nickel, ruthenium, rhodium, palladium, osmium, iridium, and platinum; and Group IB elements such as copper and silver. Among them, Group VIII elements are preferred, of which platinum group elements including ruthenium, rhodium, palladium, osmium, iridium and platinum are more preferred, and iridium is especially preferred.

Compounds of transition elements include, for example, inorganic compounds of transition elements such as elementary substances (metals), oxides, sulfides, hydroxides, halides including fluorides, chlorides, bromides, and iodides, sulfates, oxoacids containing transition elements or salts thereof, and inorganic complexes; and organic compounds of transition elements, including cyanides, salts of organic acids such as acetates, and organic complexes. Of these, organic complexes are preferred. Ligands in complexes can be any ligands. Transition elements in transition element compounds may each have a valency of about 0 to about 6, and preferably about 0 to about 3. Iridium compounds, if used, preferably have a valency of 1 or 3.

Taking iridium as an example, representative examples of transition element compounds are inorganic compounds including metal iridium, iridium oxide, iridium sulfide, iridium hydroxide, iridium fluoride, iridium chloride, iridium bromide, iridium iodide, iridium sulfate, iridic acid or salts thereof (for example, potassium iridate), inorganic iridium complexes [for example, hexaammineiridium(III) salts, and chloropentaammineiridium(III) salts]; and organic compounds including iridium cyanide, organic iridium complexes such as tris(acetylacetonato)iridium, dodecacarbonyltetrairidium(0), chlorotricarbonyliridium(I), di-μ-chlorotetrakis(cyclooctene)diiridium(I), di-μ-chlorotetrakis(ethylene)diiridium(I), di-μt-chlorobis(1,5-cyclooctadiene)diiridium(I), di-μ-chlorodichloribis(pentamethylcyclopentadienyl)diiridium(III), trichlorotris(triethylphosphine)iridium(III), pentahydridobis(trimethylphosphine)iridium(V), chlorocarbonylbis(triphenylphosphine)iridium(I), chloroethylenebis(triphenylphosphine)iridium(I), (pentamethylcyclopentadienyl)dicarbonyliridium(I), bis{1,2-bis(diphenylphosphino)ethane}iridium(I) chloride, pentamethylcyclopentadienylbis(ethylene)iridium(I), carbonylmethylbis(triphenylphosphine)iridium(I), (1,5-cyclooctadiene) (diphosphine)iridium(I) halides, 1,5-cyclooctadiene(1,2-bis(diphenylphosphino)ethane)iridium (I) hexafluorophosphate, (1,5-cyclooctadiene)bis(trialkylphosphine)iridium(I) halides, bis(1,5-cyclooctadiene)iridium tetrafluoroborate, and (1,5-cyclooctadiene) (acetonitrile)iridium tetrafluoroborate.

Preferred iridium compounds include iridium complexes, of which more preferred are organic iridium complexes. Typically preferred ligands in organic iridium complexes include unsaturated hydrocarbons such as cyclopentene, dicyclopentadiene, cyclooctene, 1,5-cyclooctadiene, ethylene, pentamethylcyclopentadiene, benzene, and toluene; nitrites such as acetonitrile; and ethers such as tetrahydrofuran. Specific examples of preferred iridium complexes include di-μ-chlorotetrakis(cyclooctene)diiridium(I), di-μ-chlorotetrakis(ethylene)diiridium(I), di-μ-chlorobis(1,5-cyclooctadiene)diiridium(I), bis(1,5-cyclooctadiene)iridium tetrafluoroborate, and (1,5-cyclooctadiene)(acetonitrile)iridium tetrafluoroborate. Each of iridium compounds can be used alone or in combination. Iridium compounds can be used in combination with compounds of other transition elements.

Other transition element compounds than iridium compounds include compounds corresponding to the iridium compounds, such as dichloro(1,5-cyclooctadiene)ruthenium, dichloro(1,5-cyclooctadiene)platinum, and dichlorobis(1,5-cyclooctadiene)dirhodium. Such other transition element compounds than iridium compounds are also preferably organic complexes. Preferred ligands herein include unsaturated hydrocarbons such as cyclopentene, dicyclopentadiene, cyclooctene, 1,5-cyclooctadiene, ethylene, pentamethylcyclopentadiene, benzene, and toluene; nitrites such as acetonitrile; and ethers such as tetrahydrofuran.

Transition element compounds can be used as intact or as catalysts supported by carriers. The carriers include those used for supporting catalysts in related art. Examples of carriers are inorganic metal oxides such as silica, alumina, silica-alumina, zeolite, titania, and magnesia; and activated carbon. In a catalyst supported by a carrier, the amount of transition element compounds is, for example, about 0.1 to about 50 percent by weight and preferably about 1 to about 20 percent by weight, relative to the carrier. A catalyst can be supported by a carrier according to any procedure such as impregnation, precipitation, or ion exchange.

The amount of transition element compounds is, for example, about 0.0001 to about 1 mole, preferably about 0.001 to about 0.3 mole, and more preferably about 0.005 to about 0.1 mole, per 1 mole of a compound represented by Formula (2) used as a reaction component.

Vinyl or Allyl Ester Compounds

Compounds represented by Formula (1) are vinyl ester compounds where "n" is 0, and are allyl ester compounds where "n" is 1. $R^1$, $R^2$, $R^3$, $R^4$, $R^5$, and $R^6$ may be the same as or different from one another and each represent hydrogen atom or a nonmetallic atom-containing group. Nonmetallic atom-containing groups can be any groups that do not adversely affect the reaction, such as organic groups that are not reactive under reaction conditions in a process according to an embodiment of the present invention. Examples of such groups are halogen atoms; hydrocarbon groups; heterocyclic groups; substituted oxycarbonyl groups such as alkoxycarbonyl groups, aryloxycarbonyl groups, aralkyloxycarbonyl groups, and cycloalkyloxycarbonyl groups; carboxyl group; substituted or unsubstituted carbamoyl groups; cyano group; nitro group; sulfur acid group; sulfur acid ester group; acyl groups including acetyl group and other aliphatic acyl groups, and benzoyl group and other aromatic acyl groups; substituted oxy groups including alkoxy groups such as methoxy group, ethoxy group, and other alkoxy groups having one to six carbon atoms, aryloxy groups, aralkyloxy groups, and cycloalkyloxy groups; N,N-disubstituted amino groups such as N,N-dimethylamino group and piperidino group; and groups each containing two or more of these groups combined with each other. The carboxyl group and other groups may be protected by protecting groups used in organic synthesis. The halogen atoms include fluorine, chlorine, bromine and iodine atoms. Of these organic groups, preferred are hydrocarbon groups and heterocyclic groups.

The hydrocarbon groups and heterocyclic groups also include substituted hydrocarbon groups and heterocyclic groups. The hydrocarbon groups include aliphatic hydrocarbon groups, alicyclic hydrocarbon groups, aromatic hydrocarbon groups, and groups containing these groups combined with each other. The aliphatic hydrocarbon groups include, for example, alkyl groups having about one to about twenty carbon atoms, such as methyl, ethyl, propyl, isopropyl, butyl, isobutyl, s-butyl, t-butyl, pentyl, hexyl, decyl, and dodecyl groups, of which those having about one to about ten carbon atoms are preferred, and those having about one to about three carbon atoms are more preferred; alkenyl groups having about two to about twenty carbon atoms, such as vinyl, allyl, and 1-butenyl groups, of which those having about two to about ten carbon atoms are preferred, and those having about two or three carbon atoms are more preferred; and alkynyl groups having about two to about twenty carbon atoms, such as ethynyl and propynyl groups, of which those having about two to about ten carbon atoms are preferred, and those having about two or three carbon atoms are more preferred.

The alicyclic hydrocarbon groups include cycloalkyl groups having about three to about twenty members, such as cyclopropyl, cyclobutyl, cyclopentyl, cyclohexyl, and cyclooctyl groups, of which those having about three to about fifteen members are preferred, and those having about five to about eight members are more preferred; cycloalkenyl groups having about three to about twenty members, such as cyclopentenyl and cyclohexenyl groups, of which those having about three to about fifteen members are preferred, and those having about five to about eight members are more preferred; and bridged hydrocarbon groups such as perhydronaphth-1-yl group, norbornyl, adamantyl, and tetracyclo[4.4.0.1$^{2,5}$.1$^{7,10}$]dodec-3-yl groups. The aromatic hydrocarbon groups include aromatic hydrocarbon groups having about six to about fourteen carbon atoms, such as phenyl and naphthyl groups, of which those having about six to about ten carbon atoms are preferred.

Hydrocarbon groups each containing an aliphatic hydrocarbon group and an alicyclic hydrocarbon group combined with each other include cycloalkyl-alkyl groups such as cyclopentylmethyl, cyclohexylmethyl, and 2-cyclohexylethyl groups, of which those having about three to about twenty carbon atoms in the cycloalkyl moiety and about one to about four carbon atoms in the alkyl moiety are preferred. Hydrocarbon groups each containing an aliphatic hydrocarbon group and an aromatic hydrocarbon group combined with each other include aralkyl groups such as aralkyl groups having about seven to about eighteen carbon atoms; alkyl-substituted aryl groups such as phenyl group or naphthyl group substituted with about one to about four alkyl groups each having about one to about four carbon atoms.

Preferred hydrocarbon groups include, for example, alkyl groups having about one to about ten carbon atoms, alkenyl groups having about two to about ten carbon atoms, alkynyl groups having about two to about ten carbon atoms, cycloalkyl groups having about three to about fifteen carbon atoms, aromatic hydrocarbon groups having about six to about ten carbon atoms, cycloalkyl-alkyl groups having about three to about fifteen carbon atoms in the cycloalkyl moiety and about one to about four carbon atoms in the alkyl moiety, and aralkyl groups having about seven to about fourteen carbon atoms.

The hydrocarbon groups may each have one or more substituents. Examples of substituents are halogen atoms; oxo group; hydroxyl group; substituted oxy groups such as alkoxy groups, aryloxy groups, aralkyloxy groups, and acyloxy groups; carboxyl group; substituted oxycarbonyl groups such as alkoxycarbonyl groups, aryloxycarbonyl groups, and aralkyloxycarbonyl groups; substituted or unsubstituted carbamoyl groups; cyano group; nitro group; substituted or unsubstituted amino groups; sulfo group; and heterocyclic groups. The hydroxyl group and carboxyl group may be protected by protecting groups for use in organic synthesis.

Rings of alicyclic hydrocarbon groups and aromatic hydrocarbon groups may have aromatic or nonaromatic heterocyclic rings fused thereto.

Heterocyclic groups constituting the heterocyclic groups in the substituents such as $R^1$ include aromatic heterocyclic groups and nonaromatic heterocyclic groups. Examples of such heterocyclic groups include heterocyclic groups containing oxygen atom as a hetero atom, including five-membered rings such as furan, tetrahydrofuran, oxazole, isoxazole, and γ-butyrolactone rings, six-membered rings such as 4-oxo-4H-pyran, tetrahydropyran, and morpholine rings, fused rings such as benzofuran, isobenzofuran, 4-oxo-4H-chromene, chroman, and isochroman rings, and bridged rings such as 3-oxatricyclo[4.3.1.1$^{4,8}$]undecan-2-one ring and 3-oxatricyclo[4.2.1.0$^{4,8}$]nonan-2-one ring; heterocyclic groups containing sulfur atom as a hetero atom, including five-membered rings such as thiophene, thiazole, isothiazole, and thiadiazole rings, six-membered rings such as 4-oxo-4H-thiopyran ring, and fused rings such as benzothiophene ring; and heterocyclic groups containing nitrogen atom as a hetero atom, including five-membered rings such as pyrrole, pyrrolidine, pyrazole, imidazole, and triazole rings, six-membered rings such as pyridine, pyridazine, pyrimidine, pyrazine, piperidine, and piperazine rings, and fused rings such as indole, indoline, quinoline, acridine, naphthyridine, quinazoline, and purine rings. The heterocyclic groups may each have one or more substituents. Such substituents include the substituents which the hydrocarbon groups may have, as well as alkyl groups including alkyl groups having about one to about four carbon atoms, such as methyl and ethyl groups; cycloalkyl groups; and aryl groups such as phenyl and naphthyl groups.

Preferred $R^1$, $R^2$, $R^3$, $R^4$, $R^5$, and $R^6$ include hydrogen atom and hydrocarbon groups such as alkyl groups having about one to about ten carbon atoms, alkenyl groups having about two to about ten carbon atoms, alkynyl groups having about two to about ten carbon atoms, cycloalkyl groups having about three to about fifteen carbon atoms, aromatic hydrocarbon groups having about six to about ten carbon atoms, cycloalkyl-alkyl groups having about three to about twelve carbon atoms in the cycloalkyl moiety and about one to about four carbon atoms in the alkyl moiety, and aralkyl groups having about seven to about fourteen carbon atoms. The substituent $R^1$ is typically preferably an alkyl group having about one to about three carbon atoms, such as methyl group, or phenyl group. The substituents $R^2$, $R^3$, $R^4$, $R^5$, and $R^6$ are each typically preferably hydrogen atom or an alkyl group having about one to about three carbon atoms, such as methyl group.

Of compounds represented by Formula (1), representative examples of vinyl ester compounds include vinyl acetate, isopropenyl acetate, 1-propenyl acetate, 2-methyl-1-propenyl acetate, 1,2-dimethyl-1-propenyl acetate, vinyl formate, vinyl propionate, and vinyl benzoate. Representative examples of allyl ester compounds include allyl acetate, 2-butenyl acetate, 1-methyl-2-butenyl acetate, 2-methyl-2-butenyl acetate, 1,2-dimethyl-2-butenyl acetate, allyl formate, allyl propionate, and allyl benzoate. Allyl ester compounds further include terpenic allyl ester compounds such as linalyl acetate, d-citronellyl acetate, geranyl acetate, neryl acetate, phytyl acetate, lupeolyl acetate; geranyl formate, neryl formate, geranyl propionate, neryl propionate; and geranyl benzoate and neryl benzoate.

A vinyl or allyl ester compound for use in an embodiment of the present invention may be formed within a reaction system before carrying out the reaction. For example, a reactant allyl ester may be formed within the relation system using a corresponding allyl alcohol [$R^5R^6C$=$C(R^4)$—$C(R^2)(R^3)$—OH] and a corresponding carboxylic acid ($R^1$—

COOH). Representative examples of the allyl alcohol include allyl alcohol, 2-buten-1-ol, 1-methyl-2-buten-1-ol, 2-methyl-2-buten-1-ol, 1,2-dimethyl-2-buten-1-ol, as well as linalool, d-citronellol, geraniol, and nerol. Typical examples of the carboxylic acid are formic acid, acetic acid, propionic acid, and benzoic acid.

Compounds Represented by Formula (2)

In a process according to an embodiment of the present invention, a compound represented by Formula (2), i.e., any of wide variety of silane compounds, silanol compounds, primary amines, and secondary amines can be used as a reaction component. Compounds represented by Formula (2) may intramolecularly have, for example, hydroxyl group, oxetane group, epoxy group, and substituted or unsubstituted silyl groups. In Formula (2), $R^7$ represents a nonmetallic atom-containing group; and Y represents a group selected from the group consisting of —Si ($R^8$) ($R^9$)—, —Si ($R^{10}$) ($R^{11}$)—O—, the left hand of which is combined with $R^7$, and —N$R^{12}$—, wherein $R^8$, $R^9$, $R^{10}$, $R^{11}$, and $R^{12}$ are the same as or different from one another and each represent hydrogen atom or a nonmetallic atom-containing group. The nonmetallic atom-containing groups as $R^7$, $R^8$, $R^9$, $R^{10}$, $R^{11}$, and $R^{12}$ can be any organic groups that do not adversely affect the reaction. They can be hydroxyl group, as well as the nonmetallic atom-containing groups as exemplified in $R^1$, $R^2$, $R^3$, $R^4$, $R^5$, and $R^6$.

Preferred nonmetallic atom-containing groups as $R^7$, $R^8$, $R^9$, $R^{10}$, and $R^{11}$ include hydrocarbon groups, heterocyclic groups, acyl groups, halogen atoms, substituted oxy groups, and hydroxyl group. The hydrocarbon groups and heterocyclic groups include the hydrocarbon groups and heterocyclic groups exemplified in $R^1$, $R^2$, $R^3$, $R^4$, $R^5$, and $R^6$. The hydrocarbon groups and heterocyclic groups further include substituted hydrocarbon groups and heterocyclic groups, and hydrocarbon groups and heterocyclic groups further having rings fused thereto. The substituents herein can be any substituents, as long as they do not adversely affect the reaction, and include the substituents which the hydrocarbon groups and heterocyclic groups as $R^1$, $R^2$, $R^3$, $R^4$, $R^5$, and $R^6$ may have. The acyl groups include aliphatic acyl groups such as acetyl group; and aromatic acyl groups such as benzoyl group. The substituted oxy groups include alkoxy groups such as methoxy group, ethoxy group, and other alkoxy groups having about one to about six carbon atoms; aryloxy groups such as phenoxy group; aralkyloxy groups such as benzyloxy group; cycloalkyloxy groups such as cyclopentyloxy group and cyclohexyloxy group; and acyloxy groups such as acetyloxy group and benzoyloxy group. When the nonmetallic atom-containing group is hydroxyl group, the hydroxyl group can be converted into a vinyl or allyl ether as a result of a reaction.

Preferred examples of the nonmetallic atom-containing group as $R^{12}$ are hydrocarbon groups, heterocyclic groups, and acyl groups. The hydrocarbon groups and heterocyclic groups include the hydrocarbon groups and heterocyclic groups exemplified in $R^1$, $R^2$, $R^3$, $R^4$, $R^5$, and $R^6$. The hydrocarbon groups and heterocyclic groups further include substituted hydrocarbon groups and heterocyclic groups, and hydrocarbon groups and heterocyclic groups further having rings fused thereto. The substituents herein can be any substituents, as long as they do not adversely affect the reaction, and include the substituents which the hydrocarbon groups and heterocyclic groups as $R^1$, $R^2$, $R^3$, $R^4$, $R^5$, and $R^6$ may have. The acyl groups include aliphatic acyl groups such as acetyl group; and aromatic acyl groups such as benzoyl group.

Representative silane compounds include trisubstituted silane compounds, disubstituted silane compounds, and monosubstituted silane compounds. The trisubstituted silane compounds include trialkylsilanes, triarylsilanes, triaralkylsilanes, dialkylmonohalosilanes, and dialkylmonoalkoxysilanes, such as trimethylsilane, triethylsilane, tripropylsilane, tributylsilane, triphenylsilane, tribenzylsilane, dimethylchlorosilane, and methoxydimethylsilane. The disubstituted silane compounds include dialkylsilanes, diarylsilanes, diaralkylsilanes, monoalkylmonohalosilanes, and monoalkylmonoalkoxysilanes, such as dimethylsilane, diethylsilane, dipropylsilane, dibutylsilane, diphenylsilane, dibenzylsilane, methylchlorosilane, and methoxymethylsilane. The monosubstituted silane compounds include monoalkylsilanes, monoarylsilanes, and monoaralkylsilanes, such as monomethylsilane, monoethylsilane, monopropylsilane, monobutylsilane, monophenylsilane, and monobenzylsilane.

Representative silanol compounds include trisubstituted silanol compounds (tertiary silanols), disubstituted silanol compounds (secondary silanols), and monosubstituted silanol compounds (primary silanols). The trisubstituted silanol compound include trialkylsilanols, triarylsilanols, triaralkylsilanols, dialkylmonohalosilanols, and dialkylmonoalkoxysilanols, such as trimethylsilanol, triethylsilanol, tripropylsilanol, tributylsilanol, triphenylsilanol, tribenzylsilanol, dimethylchlorosilanol, and methoxydimethylsilanol. The disubstituted silanol compounds include dialkylsilanols, diarylsilanols, diaralkylsilanols, monoalkylmonohalosilanols, and monoalkylmonoalkoxysilanols, such as dimethylsilanol, diethylsilanol, dipropylsilanol, dibutylsilanol, diphenylsilanol, dibenzylsilanol, methylchlorosilanol, and methoxymethylsilanol. The monosubstituted silanol compounds include monoalkylsilanols, monoarylsilanols, and monoaralkylsilanols, such as monomethylsilanol, monoethylsilanol, monopropylsilanol, monobutylsilanol, monophenylsilanol, and monobenzylsilanol.

Representative primary amines include primary amines having about one to about twenty carbon atoms. They include aliphatic primary amines, alicyclic primary amines, aromatic primary amines, and heterocyclic primary amines, such as methylamine, ethylamine, propylamine, butylamine, hexylamine, octylamine, cyclopentylamine, cyclohexylamine, aniline, benzylamine, and aminopyridine.

Representative secondary amines include secondary amines having about two to about twenty carbon atoms. They include aliphatic secondary amines, alicyclic secondary amines, aromatic secondary amines, heterocyclic secondary amines, and cyclic amines, such as dimethylamine, diethylamine, dipropylamine, dibutylamine, dihexylamine, dioctylamine, dicyclohexylamine, N-methylaniline, N-methylbenzylamine, N-methylaminopyridine, pyrrolidine, piperidine, and morpholine.

These representative compounds may each have one or more substituents within ranges not adversely affecting the reaction.

Reaction

A reaction between a vinyl or allyl ester compound represented by Formula (1) and a compound represented by Formula (2) is carried out in the presence of, or in the absence of a solvent. The solvent includes, but is not limited to, aliphatic hydrocarbons such as hexane, heptane, and octane; alicyclic hydrocarbons such as cyclohexane; aromatic hydrocarbons such as benzene, toluene, xylenes, and ethylbenzene; halogenated hydrocarbons such as chloroform, dichloromethane, and 1,2-dichloroethane; ethers such as diethyl ether, dimethoxyethane, tetrahydrofuran, and dioxane; ketones such as acetone and methyl ethyl ketone; esters such as methyl acetate, ethyl acetate, isopropyl acetate, and butyl acetate; amides such as N,N-dimethylformamide and N,N-dimethylacetamide; and nitrites such as acetonitrile, propionitrile, and benzonitrile. Each of these solvents can be used alone or in combination.

The amount of the vinyl or allyl ester compound represented by Formula (1) is, for example, about 0.8 to about 15 equivalents, preferably about 1 to about 12 equivalents, and more preferably about 3 to about 10 equivalents, per 1 equivalent of the compound represented by Formula (2). The vinyl or allyl ester compound represented by Formula (1) can be used in large excess.

A base may be incorporated in the reaction system according to an embodiment of the present invention. The base includes, for example, inorganic bases such as sodium hydroxide, sodium carbonate, and sodium hydrogen carbonate; and organic bases such as sodium acetate and sodium ethoxide. The amount of the base is, for example, about 0.01 to about 2 moles and preferably about 0.1 to about 1.5 moles, per 1 mole of the compound represented by Formula (2).

When a reactant allyl ester compound is formed within the reaction system by adding an allyl alcohol and a carboxylic acid to the system as mentioned above, the amount of the carboxylic acid is not specifically limited and is, for example, about 0.01 to about 2 moles and preferably about 0.05 to about 1 mole, per 1 mole of the allyl alcohol. A reaction can proceed even when a carboxylic acid is used in a catalytic amount. The reaction can be carried out in the presence of a dehydrating agent such as molecular sieve. The reaction can also be conducted while distilling by-produced water. Where necessary, a strong acid, such as sulfuric acid or p-toluenesulfonic acid, can be used as a catalyst.

The reaction may be conducted in the presence of a polymerization inhibitor. A reaction temperature can be appropriately set according typically to the types of reaction components and catalysts and is, for example, about 0° C. to about 200° C., preferably about 20° C. to about 150° C., and more preferably about 30° C. to about 120° C. The reaction may be carried out under normal pressure, under reduced pressure, or under a pressure (under a load). A reaction atmosphere is not limited, as long as not adversely affecting the reaction, and can be any atmosphere such as air atmosphere, nitrogen atmosphere, or argon atmosphere. The reaction can be carried out according to any system such as batch system, semi-batch system, or continuous system.

A process according to an embodiment of the present invention carries out a reaction under mild conditions to yield a corresponding vinyl- or allyl-containing silicon compound represented by Formula (3) (silyl vinyl ether or silyl allyl ether) or corresponding vinyl- or allyl-containing amine compound represented by Formula (3) (e.g., allylamine). More specifically, when a vinyl ester compound, i.e. a compound of Formula (1) wherein "n" is 0, is used as a compound represented by Formula (1), it yields a corresponding vinyl-containing compound, i.e., a compound represented by Formula (3) wherein "n" is 0. When an allyl ester compound, i.e., a compound of Formula (1) wherein "n" is 1 is used, it yields a corresponding allyl-containing compound, i.e., a compound of Formula (3) wherein "n" is 1. When a compound represented by Formula (2) is a trisubstituted silane, a trisubstituted silanol, or a secondary amine, it yields a monovinyl or monoallyl compound as a main product. When the compound represented by Formula (2) is a disubstituted silane, a disubstituted silanol, or a primary amine, it yields a divinyl or diallyl compound as a main product. When the compound represented by Formula (2) is a monosubstituted silane or a monosubstituted silanol, it yields a trivinyl or triallyl compound as a main product. When a compound intramolecularly having a hydroxyl group is used, the hydroxyl group can be converted into a vinyl ether or allyl ether, as described above.

After the completion of reaction, a reaction product can be separated and purified by a separation procedure such as filtration, concentration, distillation, extraction, crystallization, recrystallization, or column chromatography, or a combination of these separation procedures.

The resulting vinyl- or allyl-containing compounds can be used typically as semiconductor materials, raw materials for functional polymers, intermediates for the synthetic preparation of fine chemicals such as pharmaceutical preparations and agricultural chemicals, and intermediate materials for organic chemicals.

EXAMPLES

The present invention will be illustrated in further detail with reference to several examples below. It should be noted, however, that these are illustrated only by way of example and are never intended to limit the scope of the present invention.

Example 1

In a reactor were placed triethylsilane ($Et_3SiH$) (5 mmol), di-μ-chlorobis(1,5-cyclooctadiene)diiridium(I) [$IrCl(cod)$]$_2$ (0.05 mmol), vinyl acetate (20 mmol), and toluene (3 ml), and a reaction was conducted at 40° C. in a nitrogen atmosphere for one hour. After the reaction, the reaction mixture was analyzed by gas chromatography to find that vinyltriethylsilane was produced in a yield of 20%, and tetraethylsilane and acetic ester of triethylsilanol were by-produced in yields of 9% and 14%, respectively.

Example 2

In a reactor were placed di-μ-chlorobis(1,5-cyclooctadiene)diiridium(I) [$IrCl(cod)$]$_2$ (0.05 mmol), vinyl acetate (20 mmol), and toluene (3 ml). The mixture was raised in temperature to 40° C. in a nitrogen atmosphere, triethylsilane ($Et_3SiH$) (5 mmol) was added thereto over one hour, and a reaction was carried out at 40° C. for one hour. After the reaction, the reaction mixture was analyzed by gas chromatography to find that vinyltriethylsilane was produced in a yield of 36% and tetraethylsilane and acetic ester of triethylsilanol were by-produced in yields of 7% and 12%, respectively.

Example 3

A reaction was carried out by the procedure of Example 2, except for using triphenylsilane ($Ph_3SiH$) instead of triethylsilane. After the reaction, the reaction mixture was analyzed by gas chromatography to find that vinyltriphenylsilane was produced in a yield of 38%.

Example 4

In a reactor were placed triphenylsilanol ($Ph_3SiOH$) (5 mmol), di-μ-chlorobis(1,5-cyclooctadiene)diiridium(I) [$IrCl(cod)$]$_2$ (0.05 mmol), sodium carbonate (5 mmol), vinyl acetate (20 mmol), and toluene (3 ml), and a reaction was carried out at 100° C. in a nitrogen atmosphere for fifteen hours. After the reaction, the reaction mixture was analyzed by gas chromatography to find that triphenylsilyl vinyl ether ($Ph_3Si$—O-vinyl) was produced in a yield of 56%.

Example 5

A reaction was carried out by the procedure of Example 4, except for using triethylsilanol ($Et_3Si$—OH) instead of triphenylsilanol. After the reaction, the reaction mixture was analyzed by gas chromatography to find that triethylsilyl vinyl ether ($Et_3Si$—O-vinyl) was produced in a yield of 49%.

Example 6

In a reactor were placed bis(1,5-cyclooctadiene)iridium tetrafluoroborate $[Ir(cod)_2]^+BF_4^-$ (0.05 mmol), allyl acetate (20 mmol), and toluene (3 ml). The mixture was raised in temperature to 80° C. in a nitrogen atmosphere, triethylsilane ($Et_3SiH$)(5 mmol) was added thereto over one hour, and a reaction was conducted at 80° C. for one hour. After the reaction, the reaction mixture was analyzed by gas chromatography to find that allyltriethylsilane was produced in a yield of 54% and tetraethylsilane was by-produced in a yield of 5%.

Example 7

In a reactor were placed triphenylsilanol ($Ph_3SiOH$)(5 mmol), bis(1,5-cyclooctadiene)iridium tetrafluoroborate $[Ir(cod)_2]^+BF_4^-$ (0.05 mmol), allyl acetate (20 mmol), and toluene (3 ml), and a reaction was carried out at 100° C. in a nitrogen atmosphere for fifteen hours. After the reaction, the reaction mixture was analyzed by gas chromatography to find that triphenylsilyl allyl ether ($Ph_3Si$—O-allyl) was produced in a yield of 75%.

Example 8

A reaction was carried out by the procedure of Example 7, except for using triethylsilanol instead of triphenylsilanol. After the reaction, the reaction mixture was analyzed by gas chromatography to find that triethylsilyl allyl ether ($Et_3Si$—O-allyl) was produced in a yield of 70%.

Example 9

A reaction was carried out by the procedure of Example 2, except for using isopropenyl acetate instead of vinyl acetate. After the reaction, the reaction mixture was analyzed by gas chromatography to-find that triethylisopropenylsilane was produced in a yield of 11%.

Example 10

A reaction was carried out by the procedure of Example 4, except for using isopropenyl acetate instead of vinyl acetate. After the reaction, the reaction mixture was analyzed by gas chromatography to find that triphenyl(isopropenyloxy)silane was produced in a yield of 65%.

Example 11

In a reactor were placed aniline (5 mmol), bis(1,5-cyclooctadiene)iridium tetrafluoroborate $[Ir(cod)_2]^+BF_4^-$ (0.05 mmol), allyl acetate (20 mmol), and toluene (3 ml), and a reaction was carried out at 100° C. in a nitrogen atmosphere for fifteen hours. After the reaction, the reaction mixture was analyzed by gas chromatography to find that diallylphenylamine was produced in a yield of 96%.

Example 12

A reaction was carried out by the procedure of Example 11, except for using n-hexylamine instead of aniline. After the reaction, the reaction mixture was analyzed by gas chromatography to find that diallylhexylamine was produced in a yield of 78%.

Example 13

A reaction was carried out by the procedure of Example 11, except for using benzylamine instead of aniline. After the reaction, the reaction mixture was analyzed by gas chromatography to find that diallylbenzylamine was produced in a yield of 83%.

It should be understood by those skilled in the art that various modifications, combinations, subcombinations, and alterations may occur depending on design requirements and other factors insofar as they are within the scope of the appended claims or the equivalents thereof.

What is claimed is:

1. A process for the preparation of a vinyl- or allyl-containing silicon compound represented by the following Formula (3), or a divinyl-, diallyl-, trivinyl-, or triallyl-containing silicon compound,

(3)

wherein, in the above Formula (3), $R^2$, $R^3$, $R^4$, $R^5$, and $R^6$ are independently from one another a hydrogen atom or an alkyl group having one to three carbon atoms; $R^7$ is a hydrocarbon group, a heterocyclic group, an acyl group, a halogen atom, a substituted oxy group, or a hydroxyl group; Y represents a group selected from the group consisting of —$Si(R^8)(R^9)$— and —$Si(R^{10})(R^{11})$—O—, the left hand of which is combined with $R^7$, wherein $R^8$, $R^9$, $R^{10}$, $R^{11}$, and $R^{12}$ are independently from one another a hydrogen atom, a hydrocarbon group, a heterocyclic group, an acyl group, a halogen atom, a substituted oxy group, or a hydroxyl group; and n is 0 or 1, said process comprising the step of:

carrying out a reaction between a vinyl or allyl ester compound represented by the following Formula (1):

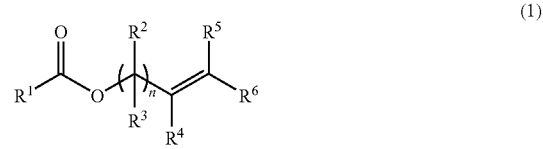

(1)

wherein $R^1$ represents an alkyl group having one to three carbon atoms or a phenyl group; $R^2$, $R^3$, $R^4$, $R^5$, $R^6$ and n are as defined above, and a compound represented by the following Formula (2):

(2)

wherein $R^7$ and Y are as defined above;

wherein the reaction is carried out in the presence of an iridium compound; and wherein a divinyl- or diallyl-containing silicon compound is prepared when the compound represented by Formula (2) is disubstituted and a trivinyl- or triallyl-containing silicon compound is prepared when the compound represented by Formula (2) is monosubstituted.

* * * * *